United States Patent [19]

Levesque et al.

[11] Patent Number: 4,767,706

[45] Date of Patent: Aug. 30, 1988

[54] FIXATION OF ENZYMES WITH BIS-DITHIOESTERS

[75] Inventors: Guy Levesque, Thaon; Jean-Louis Seris, Jurancon, both of France

[73] Assignee: Societe Nationale Elf Aquitaine, France

[21] Appl. No.: 853,639

[22] Filed: Apr. 18, 1986

[30] Foreign Application Priority Data

Apr. 19, 1985 [FR] France ................................ 85 05939

[51] Int. Cl.$^4$ ........................ C12N 11/14; C12N 11/06
[52] U.S. Cl. .................................... 435/176; 435/181
[58] Field of Search ............... 435/174, 176, 177, 180, 435/181, 179

[56] References Cited

U.S. PATENT DOCUMENTS

| | | | |
|---|---|---|---|
| 3,669,841 | 6/1972 | Miller | 435/176 |
| 4,176,006 | 11/1979 | Cormier et al. | 435/176 X |
| 4,287,345 | 9/1981 | Kotani et al. | 435/181 X |
| 4,367,309 | 1/1983 | Kondo et al. | 435/181 X |

OTHER PUBLICATIONS

Borlaza, et al., Carbohydrate Research, No. 1, vol. 68, 1979, pp. 141–143.
Borlaza, et al., Carbohydrate Research, vol. 79, 1980, pp. 125–132.
Marvel et al, J. Am. Chem. Soc. 77, pp. 5997–5999, Nov. 30, 1955.

*Primary Examiner*—David M. Naff
*Attorney, Agent, or Firm*—Ostrolenk, Faber, Gerb & Soffen

[57] ABSTRACT

Enzymes are fixed on carriers with a bis-dithioester capable of combining with the enzyme and with the carrier. The bis-dithioester has at each of its ends a group capable of reacting with an aimine function. The enzyme may be contacted with the bis-dithioester before the enzyme and carrier are combined. The carrier is an inorganic or organic solid.

16 Claims, No Drawings

FIXATION OF ENZYMES WITH BIS-DITHIOESTERS

The present invention relates to a new improved method of fixation of enzymes on solid carriers. It comprises the process of fixation, as well as the fixed enzymes so obtained.

The fixation of enzymes, that is their attachment to a solid carrier, which may be plastic, has constituted an important advance in this branch of technology. It has provided a considerable improvement, in that it allows re-use numerous times of an enzyme which otherwise, in the free state, would in practice be lost from one operation to another. Also, work with an enzyme fixed in such a way contributes to the purity of the medium treated. However, the fixation of enzymes on solid carriers, whether by adsorption or by covalent bonds, is a very delicate operation necessitating a very careful choice of materials. Fixation by covalent bonding leads to more stable systems avoiding enzyme losses during their use. However, the enzymatic system obtained by the latter method generally has a lower activity than the free enzyme alone because of steric hindrance; in effect, the fixation of a proteinic macromolecule on a rigid carrier reduces the accessibility of the substrate to be treated at the active sites of the macromolecule. It is known for example that ribonuclease fixed on agarose undergoes a reduction in activity of the order of 10 to 75% with respect to the free enzyme, depending upon the nature of the substrate treated. To remedy this defect, use can be made of a "supporting bridge", that is an intermediate reactant combining both with the carrier and with the enzyme. However, even with known systems of this kind, the enzymatic activity is generally lower than that of the free enzyme. On the other hand, the choice of agents which can act as the "bridge" is considerably restricted because many possible reactants alter the activity of the enzyme or the operative conditions which they require are not compatible with conservation of catalytic activity. The agents most frequently utilized at the present time are such as glutaraldehyde, cyanogen bromide and several others tabulated below.

| Functional Group | | |
|---|---|---|
| enzyme | carrier | Method of activation |
| —NH$_2$ | —NH$_2$ | glutaraldehyde |
| —NH$_2$ | —COOH | acyl azide carbodiimide |
| —NH$_2$ | —OH | cyanogen bromide triazines |
| —COOH | —NH$_2$ | carbodiimide |
| —OH | 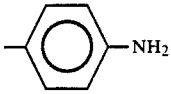—NH$_2$ | diazonium salt |
| —SH | —SH | disulphide bridge |

The majority of these agents are very delicate in use and have the disadvantages mentioned above.

The present invention brings to the technique of fixation of enzymes a considerable step forward: It utilizes a new agent, serving as a "supporting bridge", the use of which is easier and more reliable than that of the known agents indicated above; on the other hand, it provides the important advantage of producing an increased yield in the activity of the enzyme, after its fixation. Enzymatic systems formed according to the invention are very stable and easy to store at normal temperatures.

The process of fixation of an enzyme by covalent bonds according to the present invention, which utilizes a carrier comprising NH$_2$ groups and an intermediate agent fixed both to the NH$_2$ groups on the carrier as well as on the enzyme, is characterised in that the intermediate agent or "supporting bridge" is constituted by a bis-dithinic ester, the two ester functions of which are terminated by a nucleating group.

In other words, the activation agents of the carrier and the enzyme are bis-dithioesters carrying two nucleating atoms or groups capable of reacting with the NH$_2$ groups of the carrier and of the enzyme.

The invention results from the surprising discovery that the presence of dithioic groups greatly facilitates fixation of these bis-dithioesters both on the carriers and on the enzymes, without necessitating a special activation as is the case with agents of the prior art, in particular diacids or their anhydrides.

The reactant according to the invention can be represented by the formula:

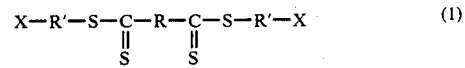

where R is a hydrocarbon chain or ring having a variable number of C atoms but preferably 1 to 20; this also applies to the R' groups; as to X, this designates an atom or group which can favour the reaction between —NH or —NH$_2$ such as for example a halogen, carboxyl, sulphinic, sulphonic, phosphorous, phosphonous, phosphoric, phosphonic, active H, SH, amide, hydroxy etc.; when R is an aliphatic chain, this can be saturated or non-saturated and most frequently comprises 2 to 18 carbon atoms and more particularly 6 to 12. This chain can carry substituents, particularly aryl groups, alkyl ethers and/or halogens. As R can be a cyclic group, it can be constituted by cycloalkanes, cycloalkenes and-/or aryls having one or two rings, but in particular C$_5$ to C$_{12}$, especially phenyl, alkylphenyls, diphenyl and all such rings carrying substituents.

A preferred group X for carrying out the invention is the carboxylic group COOH which allows reaction of the "bridge" with the carrier and the enzyme under sufficiently gentle and particularly efficaceous conditions.

By way of non-limitative examples, various bis(dithioesters of carboxyalkyl groups) or carboxyalkyl tetrathioalkanedithioates are set out below.

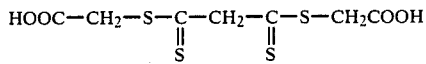

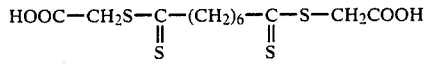

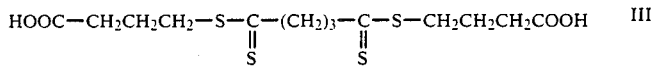 III

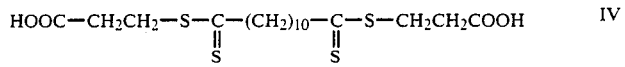 IV

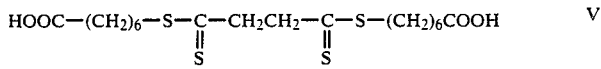 V

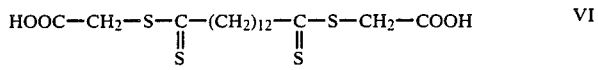 VI

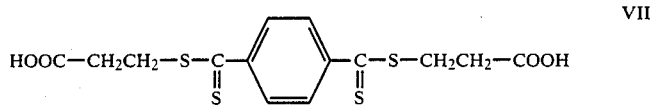 VII

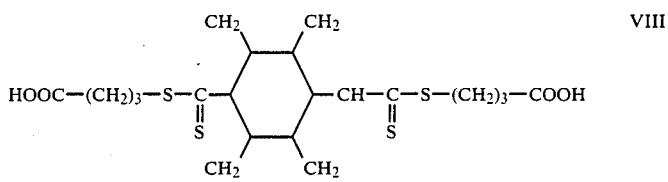 VIII

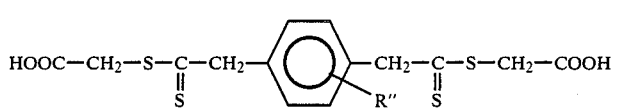 IX

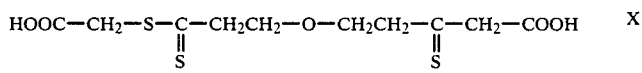 X

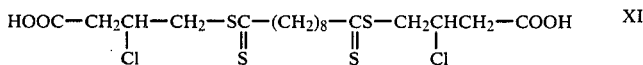 XI

In the compound IX, R" can be absent or can be formed by a substituent such as halogen, nitro, alkyl, alkoxy etc. It can also have several R" substituents.

Among the other dithioic esters which can be used for the fixation of enzymes, mention may be made of the following typical formulae:

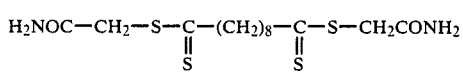 XII

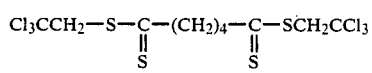 XIII

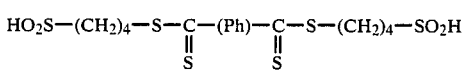 XIV

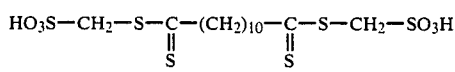 XV

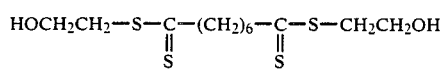 XVI

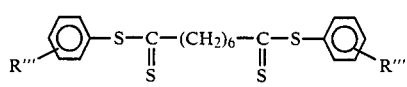 XVII

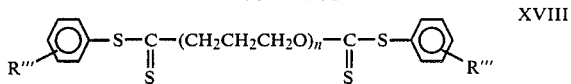 XVIII

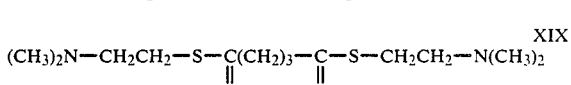 XIX

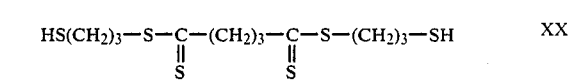 XX

These various compounds can be prepared by means of known methods such as LEVESSON (Act. Chem. Scand. part B, 29. 539, 1975), MARVEL et coll. (J. Am. Chem. Soc. 77, 5997-1955) and/or GRESSIER and LEVESQUE (Europ. Polymer. 16, 1093-1980).

From the foregoing, it can be seen that the invention allows the choice for the fixation agent of a dithioester forming a chain of greater or lesser length; it can thus serve as a "bridge" which is quite long, so that it can reduce or completely suppress steric hindrance during action of the fixed enzyme on a given substrate. Also, the properties of the fixation agent can be modified according to the uses envisaged; this can be done by the appropriate choice of the groups R, R', R", R''' and X. For example, an aromatic ring at R provides rigidity for the supporting bridge; an aliphatic chain supplies flexibility; alkoxy groups such as $-(CH_2CH_2O)_n$ and the like lead to a more or less pronounced hydrophilic property, while long $CH_2$ chains or aryls such as diphenyl tend towards hydrophobia. Thus the nucleation activity of the dithioic ester can be modified making it compatible with the fragility of a given enzyme.

The new intermediate agent according to the invention can be combined first with the carrier or with the enzyme without this undergoing any denaturation.

The carriers which can be employed are principally all those which are capable of fixing $NH_2$ groups in one manner or another or also those having a composition comprising $NH_2$ groups available for reaction with the dithioic agent. Thus, use can be made of materials such as silica, various silicates among other zeolites, glass, alumino-silicate, bentonite, as well as active aluminas and carbons treated in an appropriate manner by an amine. Also celluloses and their derivatives are suitable, particularly aminated celluloses, chitosane and above all proteins which are sufficiently rigid and carry NH or $NH_2$ groups capable of reacting with the X groups of the agent according to the invention. In this latter category, it is possible to choose an adequate carrier from materials such as, for example, casein, lactoglobulin, ovalbumin, serum albumin etc. if necessary hardened by heating or chemical action. Another class of very interesting carriers are synthetic polymers carrying free or partially combined NH groups, such as in particular polyaminopolystyrene, polyacrylamide, aminated polyacrylates, glycidyl polymethacrylate (or polyacrylate) aminated by opening of the epoxy bridges, under the action of an amine or ammonia (FR 2 442 244).

As regards the enzymes and co-enzymes suitable for the process of the invention, they apply in a general fashion to all such groups, that is to hydrolases, particularly proteases, carbohydrases and esterases as well as to oxidases, dehydrogenases, isomerization enzymes and those involving polymerisation etc. Thus with the aid of dithioesters according to the invention, fixation can be effected of amylases, arginase, dipeptidase, enolase, aldolase, adenosine, deaminase, lipases, catalases, peroxidases, glucose oxidases, galactose oxidases, lactate oxidases, oxalate oxidase, pyruvate oxidases, nuclease, ribonuclease, lysozyme, trypsin, chymotrypsine, rennet, invertase, maltase, pectinase, alcohol dehydrogenases, lactate dehydrogenase, formate dehydrogenase, glucose dehydrogenase etc.

The fixation according to the invention of enzymes can be carried out by simple contact at a low temperature, most particularly from 0° to 30° C. and especially from 0° to 10° C. of the desired enzyme with the carrier activated by the dithioester in a pH buffer suitable for the enzyme.

Preliminary activation of the carrier is generally effected by maintaining the carrier in a solution of the dithioester in a solvent. Depending upon the affinity of the dithioester for the $-NH_2$ groups of the carrier, this operation takes place cold or in the hot, generally from 0° to 100° C. and most particularly at the ambient temperature or from 10° to 35° C.

When the carrier does not naturally contain $-NH_2$ or $-NH-$, it is treated before activation with an amine. In this case, as for example with silica and silicates, the solid carrier undergoes two successive treatments; first, amination followed by separation of the aminated reactant and drying of the carrier; then contact of the latter with a solution, generally organic, of the dithioester. As regards preliminary activation of the enzyme, this principally involves the "soft" modification of the lysine residues present on the external surface of the protein.

In general, grafting of the bis-dithioester on the enzyme takes place in a medium buffered to a pH equal to or about neutrality. However, when the enzyme tolerates a slightly basic pH without disadvantage, it is of interest to operate in such a medium. This accelerates the grafting action by catalysis due to the OH ions. Thus, one of the advantageous embodiments of the invention comprises operation within a buffer of pH 7 to 9 and preferably between pH 8 and 9.

After fixation of an enzyme on the carrier by the intermediary of the bis-dithioester, usually a certain proportion of the dithioic groups remain which have not reacted; it is thus suitable to deactivate these. For this, it is suitable according to the invention to react these groups with small molecules of the type $H_2N-R-Y$, where R is an aliphatic or aryl hydrocarbon group of low molecular weight, preferably from $C_2$ to $C_8$, and Y is a functional group selected according to the properties which it will confer on the environment of the enzyme; Y can be for example $-COOH$, $-CH_2OH$, $-CH_3$ or others which are non-toxic to the activity of the enzyme.

A mode of operation of the process of the invention consists in first activating the aminated functions carried by the enzyme by means of a bis-dithioester before putting it into contact with the aminated polymer. In this case, the quantity of the reagent necessary and sufficient for this activation is first optimised in order to avoid an excess of the bis-dithioester. This way of operating is advantageous in the case of certain soluble aminated carriers, avoiding the crosslinking which can occur during direct activation of the latter.

A particular and advantageous example of the process of fixation according to the invention consists in treating a purified porous silica gel with a solution of a silane in an appropriate solvent; the silane can be an alkyl-silane, an alkyl-halosilane and preferably an alkylamino-silane. In the case where an amino-silane has not been used, the product can be treated with an amine or ammonia, after which the solid is separated, washed and dried. The silica thus pre-activated is put into suspension in an organic solution of the dithioester according to the invention; the solvent can be for example an alcohol, a ketone etc. or a mixture of solvents. Generally 0.1 to $10^{-6}$, and particularly $10^{-2}$ to $10^{-5}$ mole of the dithio ester are employed per gram of dry carrier; this quantity is determined by the content of $NH_2$ groups of the carrier, 1 mole of the dithioester being employed in principle per $NH_2$ group present.

After the required time, generally comprising 6 to 60 hours, the carrier is separated from the solvent, washed with it and then with distilled water and is then suspended in a pH buffer solution suitable for the enzyme which it is desired to fix; this suspension can be stored for a long period prior to its use.

In order to effect fixation, the desired enzyme is introduced into the suspension of the carrier within the pH buffer; the mixture is allowed to stand generally for 4 to 40 hours and most frequently from 10 to 30 hours, at the temperature indicated above, preferably around 4° to 8° C. Then the carrier is separated by filtration or centrifuging, washing with an aqueous electrolyte solution and then with the appropriate pH buffer. It is then ready to be used, but can also be stored in the selected buffer solution.

Since the bis-dithioesters described are suitable for the fixation of enzymes on plastic or pasty supports, several examples of which are cited above, they are also suitable for the preparation of enzymatic membranes or captors. In this use, the membrane can be obtained for example by the co-cross-linking of an enzyme with a protein gel, cellulose or an aminated cellulose ester or with an acrylic, styrenic or vinyl polymer carrying $NH_2$ or NH groups, by means of a bis-dithioester according to the present invention.

The invention is illustrated by the non-limitative examples which follow.

EXAMPLE 1

Fixation of glucose oxydase on a silica carrier 100 g of silica known commercially under the name XOB 30D, having an average pore diameter of 650 Å and a specific surface of 50 $m^2/g$, are first treated with a 1/1 sulpho-nitric mixture and then well rinsed with distilled water. The silica is then dried to eliminate all traces of water and is then treated for 6 hours at ambient temperature with 300 ml of a toluene solution containing 15 g of trimethoxypropylamino-silane, $(CH_3O)_3$-$SiCH_2CH_2CH_2NH_2$. The silica thus silanated and aminated is separated from the solution and then washed abundantly with toluene and then with hexane to eliminate the excess silane. It is then dried.

5 g of this dried aminated silica is then put into suspension in 50 ml of an ethanol solution of 0.177 g or 0.0005 mole ($10^{-2}$ mole/liter) of carboxymethyl tetrathiooctanedioate

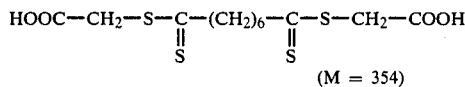

(M = 354)

The suspension, agitated from time to time, is left to stand at the ambient temperature for 48 hours. The silica is then separated from the solution, washed with ethanol and then with distilled water and introduced into a phosphate buffer solution of pH 7, in which it is stored. 1 g of the silica thus stored, with 10 ml of buffer, receive 0.020 g of glucose oxidase (GOD) of the type known under the designation II (sigma). Attachment is allowed to occur at a temperature of 5° to 6° C. After 24 hours of contact, the silica is separated by filtration, washed with 20 ml of a 1M solution of NaCl and then with 20 to 40 ml of distilled water and finally rinsed with the buffer solution in which the grafting took place. Washing of the NaCl (or M urea utilized in the other examples) has the object of eliminating the fraction of the GOD enzyme only retained by adsorption. To measure the activity of the GOD and thus confirm its fixation, the treated silica is put into contact with a 1 g/l solution of glucose and its activity is determined by spectrophotometry.

EXAMPLE 2

Determination of the enzymatic activity of glucose oxydase fixed according to Example 1

First the activity of the same quantity of the enzyme utilized for the grafting in the free state is determined in a buffer solution. This activity of the free GOD is determined at a temperature of 34°-35° C. in the free air with light agitation by simple contact between the enzyme and a solution of glucose.

The activity of the GOD grafted on the silica is determined under the same operative conditions.

| Free GOD | Grafted GOD |
|---|---|
| 20 mg GOD | 1 g of grafted silica |
| 10 ml buffer | with 20 mg of GOD, |
| x ml of glucose | 10 ml of buffer, |
| solution | x ml of glucose solution. |

The activity in one case as in the other is monitored by spectrophotometric dosages, using the hexokinase method.

The activity of the fixed GOD is practically the same as that of the free GOD determined under the same conditions.

EXAMPLE 3

Activity of the fixed enzyme as a function of time

Different determinations of the enzymatic activity are effected over several months, starting with he same sample of glucose oxidase fixed on 1.00 g of silica activated with carboxymethyl tetrathiododecanedioate grafted on to 20 mg of GOD in 10 ml of pH 7 buffer. A 5 g/l solution of β-D-glucose is added at time zero. After 1 minute, the quantity of glucose present in the suspension is determined in order to deduce the proportion of the substrate converted during this period. After six months of storage, the activity was unchanged.

EXAMPLE 4

Preliminary activation of the enzyme

Increasing quantities of a solution of the bis-dithioesters mentioned below at a concentration of $10^{-2}M$ are added to a solution of glucose oxidase in the phosphate buffer such as defined in Example 1:

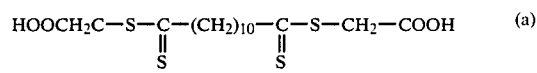

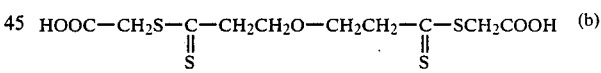

In each case, the disappearance of the dithioester function is followed by spectrophotometry at 310 nm to ensure that the reaction has taken place with the $NH_2$ accessible groups in the glucose oxidase.

A difference of the reactivity of the two compounds (a) and (b) is observed; related to the molecule of the active protein present in solution, it can be estimated that 5 is the number of activated amine functions by the compound (a) and 3.8 by the compound (b).

By maintaining for 48 hours the contact between the solution of glucose oxidase and the bis-dithioester (a), the activity of the enzyme after addition of its substrate is measured and no reduction in the activity is observed with respect to a control solution stored under the same conditions, but in the absence of the bis-dithioester.

This example shows that either the enzyme or the aminated support can be activated in the first place which allows choice for each type of enzyme of the best medium for obtaining an optimum yield.

EXAMPLE 5

Fixation of alcohol dehydrogenase 10 g of silica aminated according to the method described in Example 1 and activated with carboxymethyl tetrathiooctane-dioate is maintained for 48 hours in suspension in 100 ml of 50 mM pH 7 phosphate buffer, containing 100 mg of alcohol dehydrogenase from yeast having an activity of about 70 IU/mg.

Then a large excess of the enzyme is introduced to increase the activity of the preparation, the excess of enzyme in solution after separation of the active support being recycled for another fixation.

After 48 hours of contact at 4° C., the silica is separated and is washed successively with the phosphate buffer, distilled water, 1M NaCl and then again suspended in the phosphate buffer.

Then the suspension of silica grafted to the alcohol dehydrogenase is incubated in an 0.1M pH 7.5 solution of glycine, in order to deactivate the dithioester groups present on the silica which have not reacted with the enzyme. Then the fixed enzyme preparation is washed again with a pH 7 phosphate buffer.

This preparation has a specific activity of 11.3 IU per gram of silica; this activity is remarkably stable as shown by the results below, obtained during the course of storage of the fixed enzyme in a phosphate buffer of pH 7 at 4° C.

| Age of the preparation (days) | Specific Activity IU/g silica |
|---|---|
| 1 day | 11.6 |
| 5 days | 10.9 |
| 10 days | 11.4 |

We claim:

1. Process of fixation of an enzyme on a carrier comprising attaching the enzyme to the carrier with a bisdithioester capable of combining both with the enzyme and with the carrier, said bisdithioester having the formula

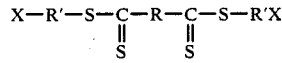

where R and R' are aliphatic, cycloaliphatic or aryl hydrocarbon groups, which can carry substituents, X being an active group capable of reacting with an amine function.

2. Process according to claim 1, wherein R is an aliphatic chain, which can contain oxygen atoms.

3. Process according to claim 1, wherein R is an aryl or alkaryl, the ring of which can carry one or more substituents.

4. Process according to claim 1, wherein R is or contains a cycloalkyl which can carry one or more substituents.

5. Process according to claim 1 wherein R' is a chain $-(CH_2)_n-$ with n equal to 2 to 18, which can carry substituents.

6. Process according to claim 1 wherein R' is an aryl, oxyaryl or alkaryl, the ring of which can carry substituents.

7. Process according to claim 1 wherein X is a carboxyl.

8. Process according to claim 1 wherein X is at least one member selected from the group consisting of halogen, hydroxyl, sulphonyl, sulphinyl and phosphoryl.

9. Process according to claim 1 in which the enzyme is at least one member of the group consisting of hydrolases, oxydoreductases, transferases, and isomerases and the carrier is an inorganic or organic solid.

10. Process according to claim 1, wherein the bisdithioester is contacted with the enzyme before the enzyme and carrier are combined.

11. Process according to claim 2 in which R contains 2 to 20 carbon atoms.

12. Process according to claim 3 in which said sisitutents are selected from the group consisting of halogen, nitro, hydroxyl and alkyl.

13. Process according to claim 4 in which R is cyclohexyl or cyclopentyl which can carry one or more alkyl, halogen, nitro or hydroxyl substituents.

14. Process according to claim 5 in which said sisitutents are selected from the group consisting of halogen, nitro, hydroxyl and alkyl.

15. Process according to claim 1 in which the carrier comprises silica and in which the bis-dithioester is

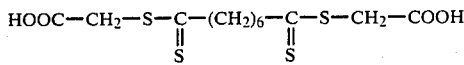

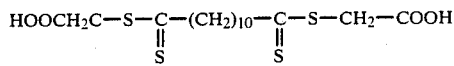

or

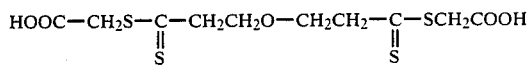

16. Process according to claim 1 wherein X is at least one member selected from the group consisting of oxygenated compounds of phosphorus, dialkylamino and mercapto.

* * * * *